United States Patent [19]

MacLauchlan et al.

[11] Patent Number: 5,449,958

[45] Date of Patent: Sep. 12, 1995

[54] DIODE EXPANDER FOR ELECTROMAGNETIC ACOUSTIC TRANSDUCER ELECTRONICS

[75] Inventors: Daniel T. MacLauchlan; Karl C. Henderson, both of Lynchburg, Va.

[73] Assignee: The Babcock & Wilcox Company, New Orleans, La.

[21] Appl. No.: 272,897

[22] Filed: Jul. 8, 1994

[51] Int. Cl.$^6$ ............................................... H02J 3/06
[52] U.S. Cl. ......................................... 307/17; 73/643
[58] Field of Search ............... 73/643; 343/13; 307/17

[56] References Cited

U.S. PATENT DOCUMENTS 3,308,561  4/1974  Sullivan et al. ..................... 333/17
4,408,493  10/1983  Peterson ............................. 73/643

Primary Examiner—William M. Shoop, Jr.
Assistant Examiner—Albert Paladini
Attorney, Agent, or Firm—Robert J. Edwards; Eric Marich

[57] ABSTRACT

An electrical circuit incorporating an improved diode expander network for an EMAT having a coil and a radio frequency power source which emits radio frequency power, and which blocks noise and interference while having the ability to operate at high frequencies and high current/power levels. A matching transformer having a primary side is operatively connected to the radio frequency source for receiving the radio frequency power. The transformer also has a secondary side having a first leg and a second leg. The matching transformer is normally a step-down transformer. A diode expander network is provided having a first pair of composite diodes connected in parallel with respect to each other to the first leg of the transformer, and a second pair of composite diodes connected in parallel with respect to each other to the second leg of the transformer. Each composite diode has a plurality of diodes arranged in a series and parallel relationship. One of the composite diodes in each pair is arranged to conduct electricity therethrough in a first direction while the other composite diode in each pair is arranged to conduct electricity therethrough in a second direction, opposite to the first direction.

10 Claims, 2 Drawing Sheets

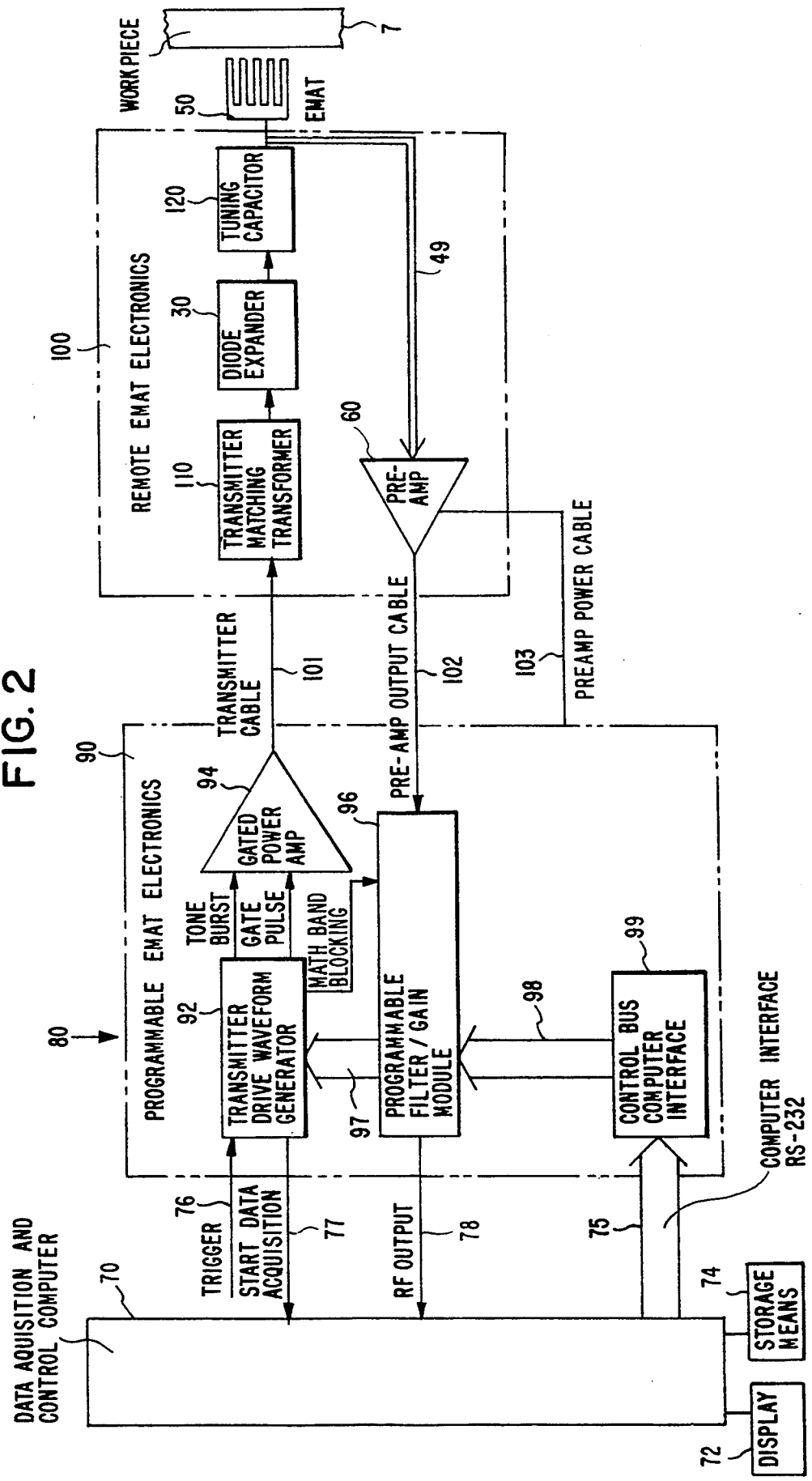

DIODE EXPANDER FOR ELECTROMAGNETIC ACOUSTIC TRANSDUCER ELECTRONICS

FIELD AND BACKGROUND OF THE INVENTION

The present invention relates, in general, to electromagnetic acoustic transducers and inspection systems utilizing same and, in particular, to a new and useful diode expander network for electromagnetic acoustic transducers.

In many systems such as radio, sonar, and ultrasonic testing systems, it is often desirable to use the same transducer or antenna for transmitting as well as for receiving. Typically, a very sensitive receiver is used, and any noise produced by the transmitter circuitry is coupled into the front end of the receiver where it is amplified and subsequently interferes with signals being picked up by the transducer or antenna. Electromagnetic acoustic transducers (EMATs) are essentially ultrasonic devices which require high energy transmitter pulses and very sensitive, low noise receivers because of the inherent low transduction efficiency.

Many devices for "disconnecting" the transmitter from the receiver, when not transmitting, have been devised including known transmit/receive (T/R) switches. A simple and very fast acting T/R switch is formed by using what is known as a diode expander to couple the transmitter to the transducer and therefore to the receiver front end. A diode expander comprises pairs of diodes connected "back to back", that is, with the anode (in electronic schematics, the broad part of the arrowhead on each diode symbol) of one diode connected to the cathode (in electronic schematics, the point of the arrowhead connected to the short crossbar on each diode symbol) of the other diode and vice versa. This arrangement allows high voltages and currents from the transmitter to pass through the diode expander with very little loss because the maximum forward voltage drop for a diode is on the order of 1 volt. Smaller noise signals in the transmitter circuitry are effectively blocked by the diodes which act like an open circuit until the turn-on voltage of the diode is exceeded. By placing diode pairs in series, the effective blocking voltage can be increased.

However, at high frequencies the junction capacitance of the diodes can effectively conduct noise signals to the receiver front end without exceeding the turn on voltage. As used herein, the term "high frequencies" refers to radio frequency (RF) level tone burst pulses in a frequency range from approximately 100–200 KHz to approximately 5–10 MHz. The junction capacitance is a parasitic capacitance between the anode and the cathode of the diode. This capacitance allows small signals which do not exceed the diode turn-on voltage to "leak" through the diode. Another limitation at high frequencies is the switching speed of the diodes. The diode switching speed is a measure of how fast the diode can switch from its conducting state to a non-conducting state when the voltage polarity across the diode reverses. The diode must be able to switch very rapidly to be used with the high frequency AC signals typically employed in EMAT applications. Further, since typical EMAT inspection systems require high current/power levels, the diodes used in circuits for such systems must have high current/power handling capability. The current handling capability of a diode is basically how much average current the diode can conduct before it overheats. Generally, as the current/power handling capability of a diode increases, the junction capacitance increases and the switching speed decreases. This has severely limited the use of the diode expander T/R switches in known EMAT applications.

Presently, there is no known diode expander circuit which provides efficient noise blockage for EMAT applications which operate at high frequencies and with high current/power levels.

SUMMARY OF THE INVENTION

The present invention pertains to transmit/receive (T/R) switches used in conjunction with electromagnetic acoustic transducers (EMATs). Accordingly, one aspect of the present invention is drawn to an electrical circuit incorporating an improved diode expander network for an EMAT having a coil and a radio frequency power source which emits radio frequency power, and which blocks noise and interference while having the ability to operate at high frequencies and high current/power levels.

The circuit comprises a matching transformer having a primary side operatively connected to the radio frequency source for receiving the radio frequency power. The transformer also has a secondary side having a first leg and a second leg. The matching transformer is normally a step-down transformer.

A diode expander network is provided having a first pair of composite diodes connected in parallel with respect to each other to the first leg of the transformer, and a second pair of composite diodes connected in parallel with respect to each other to the second leg of the transformer. Each composite diode has a plurality of diodes arranged in a series and parallel relationship. One of the composite diodes in each pair is arranged in to conduct electricity therethrough a first direction while the other composite diode in each pair is arranged to conduct electricity therethrough in a second direction, opposite to the first direction.

Another aspect of the present invention is drawn to an electromagnetic acoustic transducer inspection system for characterizing a condition of a workpiece which incorporates the improved diode expander network described above.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

BRIEF DESCRIPTION OF THE DRAWINGS

In the drawings:

FIG. 2 is a schematic block diagram illustrating an electromagnetic acoustic transducer inspection system incorporating the diode expander network of the present invention.

DESCRIPTION OF THE PREFERRED EMBODIMENT

Figure 1:
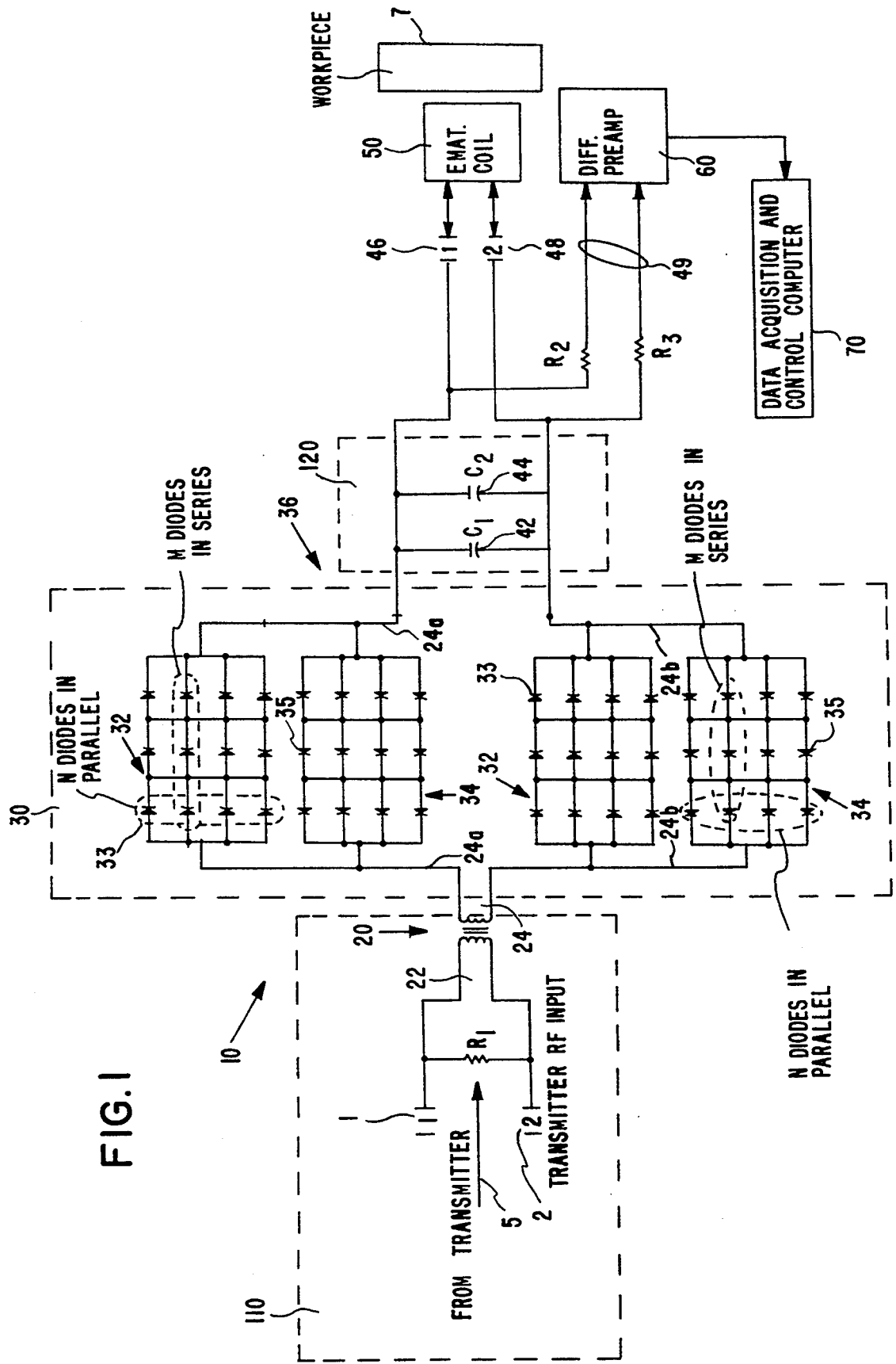
FIG. 1 is a schematic diagram illustrating the improved diode expander network of the present invention.

Referring to the drawings generally, wherein like numerals designate the same or functionally similar elements throughout the several drawings, and to FIG. 1 in particular, one aspect of the present invention is drawn to an electrical circuit incorporating an improved diode expander network for an electromagnetic acoustic transducer (EMAT) having a coil and a radio frequency (RF) power source, generally designated 10, which receives a high power, high frequency RF tone burst pulse 5 from an RF power source, such as a gated power amplifier, at input terminals 1 and 2. A matching transformer 20 is operatively connected to terminals 1 and 2 at a primary side 22 of the transformer 20, and a resistance $R_1$ is connected across the primary side 22 of the transformer 20 to provide resistive loading of cables which conduct the RF tone burst to remote electronics associated with the EMAT. The magnitude of resistance $R_1$ is typically 1 KΩ when used with 50Ω output RF power sources. This value is large enough to prevent significant loading of the transmitter pulse and small enough to prevent noise picked up on the transmitter cable from becoming large enough to couple into the front end of a differential preamplifier 60, discussed infra. Transformer 20 has a secondary side 24 opposite the primary side 22 for transferring the RF power across legs 24a and 24b. A diode expander network 30 having a very particular arrangement of composite diodes 32, 34 and arranged in pairs for each leg 24a and 24b, is operatively connected to each leg 24a and 24b of the secondary side 24 of the matching transformer 20 and, in turn, is operatively connected to EMAT coil 50 through output terminals 46 and 48.

Composite diodes 32 and 34 each comprise a plurality of very fast switching, very low capacitance diodes 33 and 35, respectively, arranged in a series and parallel relationship which allows the high power RF tone burst pulses to be coupled to the EMAT coil 50 with little attenuation. Diodes 33 and 35 are identical types of diodes; the different designations are namely being used to identify their different cathode/anode orientations in the Figures. Preferably, diodes 33, 35 are typically 1N914A silicon, fast switching diodes. These diodes have the following characteristics:

Junction Capacitance: 1.5 picofarad @ 2 Volts (reverse)

Maximum Average Rectified Current @ 25° C. (junction temperature): 200 mA

Forward voltage Drop: 1.0 Volt @ 20 mA forward current

Maximum Reverse Voltage: 100 Volt min.

Other diodes can be substituted for the preferred type, so long as their particular electrical properties are closely matched to those set forth above. Composite diodes 32 and 34 provide a high level of blocking to noise signals which are associated with the high power, radio frequency tone burst pulses 5 provided via transformer 20 of circuit 10.

20 Each composite diode 32, 34 is comprised of N diodes 33, 35 arranged in parallel with respect to each other and M diodes 33, 35 arranged in series with respect to each other, yielding a total of (N×M=T) diodes in each composite diode 32, 34. Thus, each composite diode 32, 34 has a plurality of diodes 33, 35 arranged in a series and parallel relationship in order to increase noise blocking efficiency. In a preferred embodiment, each composite diode 32, 34 is comprised of N=4 and M=3 diodes, for a total of T=12 diodes. By locating one pair of composite diodes 32 and 34 in each leg 24a and 24b of the secondary side 24 of transformer 20, the noise blocking voltage is increased and the circuit 10 is provided with symmetry for good common mode noise rejection.

Tuning capacitors $C_1$ and $C_2$ (42, 44 respectively) are operatively connected in parallel inbetween the legs 24a and 24b at an output side 36 of the composite diodes 32 and 34 and inbetween the output terminals 46 and 48. Tuning capacitors 42, 44 are provided to resonate the inductance of the EMAT coil at the desired frequency of operation, and have desired values to achieve such resonance. A differential preamplifier 60 is operatively connected to the output terminals 46 and 48 via lines 49 of the circuit 10 for receiving coil signals from EMAT coil 50. The preamplifier 60 provides amplification (perhaps a boost of 100×) of EMAT the coil 50 signals prior to being sent to a data acquisition and control computer means 70. Intermediate resistances $R_2$ and $R_3$ are provided in lines 49 and are power limiting resistors which prevent the transmitter pulse from being directly fed into the preamplifier 60 input. The magnitudes of resistances $R_2$ and $R_3$ are typically selected to have a value of 50Ω with a power rating of 1–2 watts. Data acquisition and control computer means 70 controls the settings of various parameters related to the EMAT inspection system utilizing the improved diode expander network 30 of the present invention, as well as providing for initiation of the RF tone bursts and receipt, processing, and display and/or storage of the received signals.

When transmitting, a large RF tone burst pulse 5, typically 1000 V peak to peak, is applied to circuit 10 at the primary side 22 of matching transformer 20. The tone burst pulse from the secondary side 24 of the transformer 20 is conducted through the composite diodes 32 and 34 of the diode expander network 30 to the EMAT tuning capacitors 42 and 44 and thence to the EMAT coil 50. A typical voltage on the secondary side 24 of the matching transformer 20 is 500 V peak to peak. The voltage drop across any of the individual diodes 33 and 35 is approximately one volt each for a total drop of approximately 3 V peak across the arrangement of N=4; M=3 diodes in a composite diode 32 or 34 shown in FIG. 1. This results in less than a 3% total loss in transmitter tone burst voltage. When the transmitter is off, small noise signals can be produced in the transmitter circuit 10 and by ultrasonic vibrations in the cores of the matching transformer 20 set up by the transmit tone burst pulse 5. These noise signals are blocked by the pairs of composite diodes 32, 34 of the diode expander network 30 from reaching the input to the preamplifier 60.

While diode expander networks, per se, are known in the art, conventional diode expander networks (which typically consist of just a single diode or a pair of diodes connected back-to-back or in series) are inadequate for the present EMAT applications because they are incapable of providing adequate noise rejection and current handling capability at the high frequencies involved.

The heart of the diode expander network 30 shown in FIG. 1 is the arrangement of pairs of composite diodes 32, 34 connected in each leg 24a and 24b of the circuit 10. As is known to those skilled in the art, a diode conducts current only in one direction. For current to flow through a diode, the voltage on the anode (broad part of the arrowhead on each diode in the schematic of FIG. 1) must be higher than the voltage on the cathode (the point of the arrowhead connected to the short crossbar on each diode in the schematic of FIG. 1), by 0.6 V to 1.0 V (at least for silicon diodes), depending upon the magnitude of the current. This is known as the turn-on voltage of the diode. This feature of the diode can be used to stop small signals from passing through the diodes while allowing large signals to pass through the diodes. This is the fundamental basis for the diode expander network 30 of the present invention.

For passing alternating current (AC) signals, a pair of diodes can be connected back-to-back to-back as discussed above; i.e., with the cathode of one connected to the anode of the other. Now, if the turn-on voltage is exceeded in either the positive or the negative direction, current is conducted through one or the other diode.

The characteristics of the individual diodes determines how well the diode switch will work. For EMAT applications, the main characteristics of interest are: junction capacitance, switching speed, and maximum current handling capability. As discussed earlier, the junction capacitance is a parasitic capacitance between the anode and the cathode of the diode. This capacitance allows small signals which do not exceed the diode turn-on voltage to "leak" through the diode. To minimize the amount of these small signals which "leak" through the diode (i.e., noise), the junction capacitance should be as small as possible. The diode switching speed is a measure of how fast the diode can switch from its conducting state to a non-conducting state when the voltage polarity across the diode reverses. The diode must be able to switch very rapidly to be used with the high frequency AC signals typically employed in EMAT applications. The current handling capability is basically how much average current the diode can conduct before it overheats. In general, as the current handling capability of a diode increases, the junction capacitance increases and the switching speed decreases.

Because EMATS operate with electrical currents in a range of 20 to 80 amps peak-to-peak, diodes with large maximum current handling capability are required; levels presently unavailable with any single, commercially available diode. The present invention achieves the desired characteristics needed for EMAT applications by connecting several (i.e., N) small, high switching speed, low junction capacitance diodes 33, 35 in parallel with respect to each other (that is, with the anodes of all the N diodes connected together and all of the cathodes connected together) to create a "partial" composite diode 32, 34 which has N times the maximum current handling capability of an individual diode, where N is the number of diodes connected in parallel in the composite diode 32, 34. The term "partial" as used here means only one group (M=1) of N diodes arranged in parallel. However, the high speed switching capability of the overall diode expander network 30 remains basically the same as that of an individual one of these diodes 33, 35. The need for additional groups (M>1) of N diodes is discussed below.

The junction capacitance of the individual diodes 33, 35 is combined such that the junction capacitance of the composite diode 32, 34 is (N/M) times the junction capacitance of an individual diode 33, 35, where N is the number of diodes 33, 35 connected together in parallel with respect to each other in the composite diode 32, 34 and M is the number of diodes 33, 35 connected together in series with respect to each other in the composite diode 32, 34. FIG. 1 shows what is meant by the particular groupings of N diodes connected together in parallel and M diodes connected together in series in each composite diode 32, 34; these groupings are circled and labeled as such. The resulting composite diode 32, 34 has high current handling capability, rapid switching speed, but a fairly high junction capacitance. As discussed earlier, this latter aspect is undesirable due to the increased potential for small signals to "leak" through the diodes causing noise. To counteract this aspect, several (i.e., M>1) parallel groups of diodes 33, 35 are connected together in series with respect to each other (that is, with the cathode of one diode connected to the anode of the next diode) which significantly increases the noise blocking capability of the diode expander network 30. The turn-on voltage of the series combination of M diodes is equal to M times the turn-on voltage of an individual diode 33, 35, where M is the number of diodes 33, 35 connected together in series with respect to each other in the composite diode 32, 34. Significantly, placing the diodes 33, 35 in series causes the junction capacitance of the total combination and number of diodes (N×M=T diodes), to be 1/M the value of the junction capacitance of N diodes 33, 35 arranged in parallel.

Thus it will be seen that by first connecting several (N>1) high switching speed diodes 33, 35 in parallel and then connecting several (M>1) of these parallel groups of diodes 33, 35 together in series, a diode expander network 30 or diode switch is created which can be tailored to any particular EMAT application as far as switching speed (i.e., frequency of operation), turn-on voltage (i.e., noise blocking capability), and junction capacitance leakage are concerned.

In summary, several high switching speed diodes are connected together in parallel to increase the maximum current handling capability of the diode expander network. Several of these parallel groups of diodes are then connected together in series to create a composite diode which has increased noise blocking capability and reduced the junction capacitance leakage. Finally, two of these parallel/series composite diodes are then connected "back-to-back" for AC signal operation. One pair is placed in each leg of the EMAT systems transmitter secondary to further increase the noise blocking capability, while maintaining the symmetry of the overall circuit for use with the differential preamplifier.

Another aspect of the present invention is drawn to an electromagnetic acoustic transducer inspection system for characterizing a condition of a workpiece which incorporates the diode expander network of the present invention, and is shown in FIG. 2. The characterization of a condition of a workpiece is used in its broadest aspects; testing the workpiece for the presence of flaws, cracks or inclusions; determination of thickness or other dimensions; and in certain applications can involve a determination of the metallurgical properties of the workpiece itself.

It will be appreciated that the electromagnetic acoustic inspection system according to the present invention includes many conventional components whose identity and function are well known to those skilled in the art; as such, the functions of such components will only be discussed to the extent necessary to facilitate understanding of the unique and unobvious features of the present invention. FIG. 2 discloses an electromagnetic acoustic inspection system 80 for characterizing a condition in a workpiece 7. The system 80 is comprised of four main portions: the data acquisition and control computer means 70; programmable EMAT electronics 90; remote EMAT electronics 100; and the EMAT coil 50. The data acquisition and control computer means 70 is operative to control the settings of various parameters related to the EMAT inspection system, and also serves as the primary operator interface with the system 80. Included therein would be means for digitizing the signals and processing them through known software. Accordingly, data acquisition and control means 70 could comprise a typical personal computer adapted for these purposes. Integral or connected thereto will typically be means for displaying received ultrasonic signals 72 from the workpiece 7, as well as data storage means 74 for retaining the signals as data for later analysis. A computer interface 75 is provided between data acquisition and control computer means 70 and the programmable EMAT electronics 90; a trigger signal is sent via line 76 to the electronics 90, while data acquisition start signals and RF output signals are sent via lines 77 and 78, respectively.

The programmable EMAT electronics 90 provides the means for generating a high power, high frequency, RF tone burst pulse. Electronics 90 includes a transmitter drive waveform generator 92 whose output is sent to a gated power amplifier 94. Control of the amplification and various desired waveform parameters in the RF tone burst pulse, as well as noise reduction, are accomplished in programmable filter/gain module 96, connected to generator 92 via line 97. Amplification in module 96 could again be in the order of 100×. Overall control of the programmable EMAT electronics 90 is accomplished via line 98 and control bus computer interface 99 which is connected to the data acquisition and control computer means 70 via computer interface 75.

The remote EMAT electronics 100 are connected to the programmable EMAT electronics via lines or cables 101, 102, and 103. Cable 101 conveys the high power, high frequency, RF tone burst pulse to the transmitter matching transformer 110, while cable 102 conveys the received signals from the differential preamplifier 60 to the programmable filter/gain module. Power cable 103 provides power from a power supply (not shown) in the programmable EMAT electronics 90 to the differential preamplifier 60. The transmitter matching transformer 110 would be the same as that used and discussed earlier in connection with FIG. 1,; i.e., it has a primary side and a secondary side, the primary side of the matching transformer 110 being operatively connected to the means for generating the high power, high frequency RF tone burst pulse for receiving the pulse. While the particular interconnections in the remote EMAT electronics 100 shown in FIG. 2 are simplified to single lines for clarity, the secondary side would again have a first leg and a second leg.

As was the case with the circuit of FIG. 1, diode expander network means 30 are provided for providing efficient noise blockage while operating with the high power, high frequency RF tone burst pulse. The diode expander means includes a first pair of composite diodes connected in parallel with respect to each other to the first leg of the transformer 110, and a second pair of composite diodes connected in parallel with respect to each other to the second leg of the transformer 110. Again, each composite diode has a plurality of diodes arranged in a series and parallel relationship, one of the composite diodes in each pair being arranged to conduct electricity therethrough in a first direction while the other composite diode in each pair is arranged to conduct electricity therethrough in a second direction, opposite to the first direction. Tuning capacitor means 120 again interconnect the diode expander means 30 with the EMAT coil 50; the specific interconnections would be as shown in FIG. 1. Lines 49 would convey received ultrasonic pulses generated in the workpiece 7 to the differential preamplifier 60 and eventually to the data acquisition and control computer means 70 for processing the received ultrasonic signals to characterize a condition of the workpiece 7.

While specific embodiments of the invention have been shown and described in detail to illustrate the application of the principles of the invention, it will be understood that the invention may be embodied otherwise without departing from such principles. All such embodiments have been deleted herein for the sake of conciseness and simplicity but properly fall within the scope of the following claims.

We claim:

1. An electrical circuit incorporating an improved diode expander network for an electromagnetic acoustic transducer having a coil and a radio frequency power source, the circuit comprising:

a matching transformer having a primary side and a secondary side, the primary side of the matching transformer operatively connected to the radio frequency power source for receiving the radio frequency power, the secondary side having a first leg and a second leg; and a diode expander network having a first pair of composite diodes connected in parallel with respect to each other to the first leg of the transformer, and a second pair of composite diodes connected in parallel with respect to each other to the second leg of the transformer, each composite diode having a plurality of diodes arranged in a series and parallel relationship, one of the composite diodes in each pair being arranged to conduct electricity therethrough in a first direction while the other composite diode in each pair is arranged to conduct electricity therethrough in a second direction, opposite to the first direction.

2. The circuit according to claim 1, including tuning capacitor means operatively connected between the diode expander network and the coil of the electromagnetic acoustic transducer.

3. The circuit according to claim 1, wherein the matching transformer is a step-down transformer.

4. The circuit according to claim 2, including differential preamplifier means operatively connected between the tuning capacitor means and the coil of the transducer.

5. The circuit according to claim 4, including resistor means operatively connected between the tuning capacitor means and the differential preamplifier means.

6. The circuit according to claim 4, including data acquisition and control computer means operatively connected to the differential preamplifier means.

7. An electromagnetic acoustic transducer inspection system for characterizing a condition of a workpiece, comprising:

means for generating a high power, high frequency, RF tone burst pulse;

means for providing the tone burst pulse to an EMAT coil matching network;

a matching transformer having a primary side and a secondary side, the primary side of the matching transformer operatively connected to the means for generating the high power, high frequency RF tone burst pulse for receiving the pulse, the secondary side having a first leg and a second leg;

diode expander network means for providing efficient noise blockage while operating with the high power, high frequency, RF tone burst pulse, the diode expander means including a first pair of composite diodes connected in parallel with respect to each other to the first leg of the transformer, and a second pair of composite diodes connected in parallel with respect to each other to the second leg of the transformer, each composite diode having a plurality of diodes arranged in a series and parallel relationship, one of the composite diodes in each pair being arranged to conduct electricity therethrough in a first direction while the other composite diode in each pair is arranged to conduct electricity therethrough in a second direction, opposite to the first direction;

means for transmitting the high power, high frequency RF tone burst pulse into the workpiece to create an ultrasonic pulse in the workpiece and produce ultrasonic signals in the workpiece;

means for receiving ultrasonic signals from the workpiece; and data acquisition and control computer means for processing the received ultrasonic signals from the workpiece to characterize the condition of the workpiece.

8. The system according to claim 7, wherein the data acquisition and computer control means is operative to control the settings of various parameters related to the EMAT inspection system.

9. The system according to claim 7, wherein the data acquisition and computer control means is operative to initiate the RF tone burst pulse.

10. The system according to claim 7, wherein the data acquisition and computer control means includes means for displaying the received ultrasonic signals from the workpiece.

* * * * *